US008576279B2

(12) United States Patent
Fiegler

(10) Patent No.: US 8,576,279 B2
(45) Date of Patent: Nov. 5, 2013

(54) INSPECTION DEVICE AND INSPECTION METHOD FOR DETECTING FOREIGN BODIES IN A FILLED CONTAINER

(75) Inventor: Rudolf Fiegler, Regensburg (DE)

(73) Assignee: KRONES AG, Neutraubling (DE)

( * ) Notice: Subject to any disclaimer, the term of this patent is extended or adjusted under 35 U.S.C. 154(b) by 337 days.

(21) Appl. No.: 12/846,024

(22) Filed: Jul. 29, 2010

(65) Prior Publication Data
US 2011/0025840 A1 Feb. 3, 2011

(30) Foreign Application Priority Data

Jul. 31, 2009 (DE) .......................... 10 2009 035 585

(51) Int. Cl.
*H04N 13/00* (2006.01)

(52) U.S. Cl.
USPC ........................................................ 348/127

(58) Field of Classification Search
USPC .................................................. 348/125–129
See application file for complete search history.

(56) References Cited

U.S. PATENT DOCUMENTS

| 5,180,941 | A | * | 1/1993 | Seki et al. ................. 310/323.07 |
| 5,647,931 | A | * | 7/1997 | Retallick et al. ............. 156/73.6 |
| 5,880,359 | A | | 3/1999 | Kono et al. |
| 7,372,562 | B2 | | 5/2008 | Islam et al. |
| 7,553,064 | B2 | * | 6/2009 | Johnson et al. ................ 366/109 |
| 2001/0029972 | A1 | * | 10/2001 | Kajiura et al. .................. 134/72 |
| 2001/0033372 | A1 | | 10/2001 | Dragotta |
| 2006/0283363 | A1 | * | 12/2006 | Wollman et al. ................ 111/15 |
| 2008/0001104 | A1 | * | 1/2008 | Voigt et al. ............... 250/559.46 |
| 2008/0204885 | A1 | * | 8/2008 | Ukelis et al. .................. 359/599 |
| 2008/0291438 | A1 | * | 11/2008 | Akkerman et al. ........ 356/240.1 |
| 2009/0279082 | A1 | * | 11/2009 | Till et al. .................... 356/240.1 |

FOREIGN PATENT DOCUMENTS

| DE | 102004051961 A1 | 5/2006 |
| FR | 2140808 A5 | 1/1973 |
| JP | 63311957 A | 12/1988 |
| JP | 06160305 A | 6/1994 |
| JP | 2001-059822 | * 3/2001 |
| JP | 2001059822 A | 3/2001 |
| JP | 2009115580 A | 5/2009 |
| WO | WO-0201207 A1 | 1/2002 |
| WO | WO-2004053471 A1 | 6/2004 |

OTHER PUBLICATIONS

Japanese Office Action for P2010-170644, dated Apr. 24, 2012.

* cited by examiner

*Primary Examiner* — David Czekaj
*Assistant Examiner* — Md Haque
(74) *Attorney, Agent, or Firm* — Marshall, Gerstein & Borun LLP

(57) ABSTRACT

An inspection device and an inspection method for detecting foreign bodies in a filled container, and having at least one inspection camera, a transport device for the at least section-by-section linear transport of the container and at least one vibration device for vibrating the container, where foreign bodies in the containers can be set in motion without complicated acceleration and retarding of the container and the movements can be registered and compared as single images by the inspection cameras even with a stationary camera position. The construction of the device is less space-consuming and less complicated than for machines of the rotary type and the detection of foreign bodies is more reliable than with conventional machines of the linear type.

13 Claims, 2 Drawing Sheets

INSPECTION DEVICE AND INSPECTION METHOD FOR DETECTING FOREIGN BODIES IN A FILLED CONTAINER

CROSS-REFERENCE TO RELATED APPLICATION

The present application claims the benefit of priority of German Application No. 102009035585.5, filed Jul. 31, 2009. The entire text of the priority application is incorporated herein by reference in its entirety.

FIELD OF THE DISCLOSURE

The disclosure relates to an inspection device and an inspection method for detecting foreign bodies in a filled container, such as in beverage bottling operations.

BACKGROUND

During beverage bottling in containers, such as for example glass or plastic bottles, it may be necessary to inspect the filled and sealed containers for the presence of foreign bodies. Here, it is particularly difficult to detect small particles such as transparent glass splinters. Since the containers often have scuff marks or scratches on the bottom, glass splinters can often not be clearly identified.

With regard to this problem it is known from WO 2004/053471 A1 that the content in the bottle can be set into motion on a first carousel by rotation followed by rapid retardation of the bottle and a dark field image of the bottle bottom is obtained from below while the bottle content is still in motion. The foreign bodies, which appear brightly in the image, can be acquired by stationary cameras or cameras which rotate with the bottle. Although devices of this nature can also detect small particles reliably, they are however very complex and space-consuming. In addition, they are only suitable for rotationally symmetrical bottles.

In order to avoid the outlay in terms of apparatus and time for the rotation and retardation of the bottles to be inspected, DE 10 2004 051 961 A1 suggests that the bottle content is set into motion by a vibration device. However, this device is also designed as a rotary machine with infeed and discharge stars. Additionally, a camera is needed for each bottle position on the carousel.

WO 02/01207 A1 describes an inspection device conceived for a straight-line configuration which rotates the containers in a belt station and then guides them past a row of cameras positioned at the side. These cameras supply triggered single images which are compared in an evaluation unit. However, it is difficult to quickly accelerate the bottles and retard them again and to guide them precisely in the belt station, which means that foreign matter cannot be detected with sufficient reliability and accuracy.

SUMMARY OF THE DISCLOSURE

Therefore, an aspect of the disclosure is to provide a compact inspection device with a high detection accuracy and simple construction as well as an appropriate inspection method.

This is achieved with a device with at least one inspection camera, one transport device for at least section-by-section linear transport of the container and at least one vibration device for vibrating the container.

Due to the fact that the container can also in particular be vibrated sideways in a linear machine, foreign bodies in the container are set into motion without complicated accelerating and retarding of the container. These foreign bodies can be registered in single images by the inspection camera even with a stationary camera position and detected by comparison of the images. In this way the space-consuming and complicated constructions usual with machines of the rotary type are not needed. The proportion of incorrect negative examination results is in comparison to conventional inspection devices noticeably reduced with the linear type.

Preferably, the vibration device comprises at least one vibrator for producing vibrations and a circumferentially running transmission belt for transferring the vibrations to the container. This facilitates an effective transfer of vibrations to the container side wall moving past the vibrator.

Preferably the vibrator is a motor with an unbalance. In this way vibrations can be generated in a simple and economic manner and optionally a plurality of vibrators can be combined in one vibration device.

With a particularly favorable embodiment the vibration device comprises a slide rail and/or a roller unit which is in contact with the vibrator and the transmission belt. In this way the vibrator can be arranged stationary, vibrations transferred to the passing belt and the frictional forces acting on the transmission belt can be minimized.

Preferably at least two vibration devices are provided which act on the container side wall from essentially opposite directions. In this way the transfer of vibrations to the container is particularly effective.

In a particularly favorable embodiment the transport device comprises an upper and a lower pair of guide belts which hold the container off the ground in each case and the vibration device is set up such that it transfers vibrations to the container between at least one upper and one lower guide belt. In this way the vibration device can be integrated in a simple and space-saving manner in an off-floor transport device of the linear type.

Preferably the guide belts have a damping effect on the vibration at an oscillation frequency of the vibration device. This prevents an unwanted transfer of the vibrations to the base frame of the inspection device.

Preferably the inspection camera is arranged such that it can take dark-field images of the container bottom from below. This facilitates a particularly high contrast display of foreign bodies and ensures a defined optical examination plane.

In a particularly favorable embodiment at least two inspection cameras are arranged one behind the other with respect to the transport direction of the transport device, whereby the image regions of the inspection cameras overlap. In this way a contiguous sequence of individual images can be produced, whereby changes on the container bottom during the comparison of the single images indicate moving foreign bodies.

A preferred embodiment also comprises at least one illumination device, which irradiates the container sidewards below the vibration device, in particular below the transport device. In this way foreign bodies can be particularly effectively irradiated and rendered visible through beam deflection on the foreign bodies.

Preferably the illumination device is a continuous light source. In this case the camera can be triggered independently of the light source in order to optimize the image acquisition.

Preferably at least two illumination devices are provided which form a light corridor illuminating the container on both sides. The container bottom can in this way be particularly evenly illuminated.

A particularly favorable embodiment comprises furthermore an evaluation unit for detecting the foreign bodies through the comparison of image data from the inspection camera and a diversion device for diverting faulty containers. In this way it can be ensured that only fault-free containers are processed further.

The problem is furthermore solved by an inspection method comprising the following steps: a) at least section-by-section linear transport of the container; b) sideways vibration of the container to set the foreign bodies located on the container bottom in motion; and c) image-generating acquisition of light which has been deflected by the foreign bodies.

Due to the fact that the containers are vibrated sideways in a linear machine, foreign bodies on the container bottom can be moved without complicated acceleration and retarding of the container and they can also be registered as single images and compared by inspection cameras even in a stationary camera position. In this way the space-consuming and complicated constructions usual with machines of the rotary type are not needed.

Preferably, in step c) triggered single shots of the container bottom are taken in the dark field and the method also comprises the following step: d) evaluation of the acquired image data, whereby an evaluation region is assigned to the container bottom in the single shots in each case and image data from the assigned evaluation regions are compared with one another to detect foreign bodies as differences in the compared image data; and e) rejection of the container if at least one foreign body has been found in it.

In this way a high contrast display of the foreign bodies is facilitated. In addition, the time required for the evaluation of the image data is reduced and thus the number of single images possible per inspection can be increased in favor of an improved detection probability and accuracy.

BRIEF DESCRIPTION OF THE DRAWINGS

A preferred embodiment is illustrated in the drawings. The following are shown.

DETAILED DESCRIPTION OF THE PREFERRED EMBODIMENT

Figure 1:
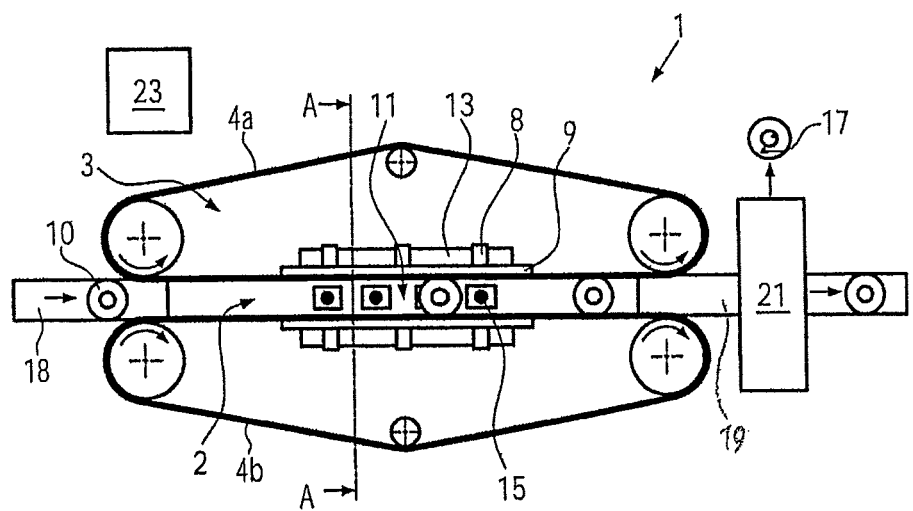
FIG. 1 a schematic plan view of an inspection device according to the disclosure.
Figure 2:
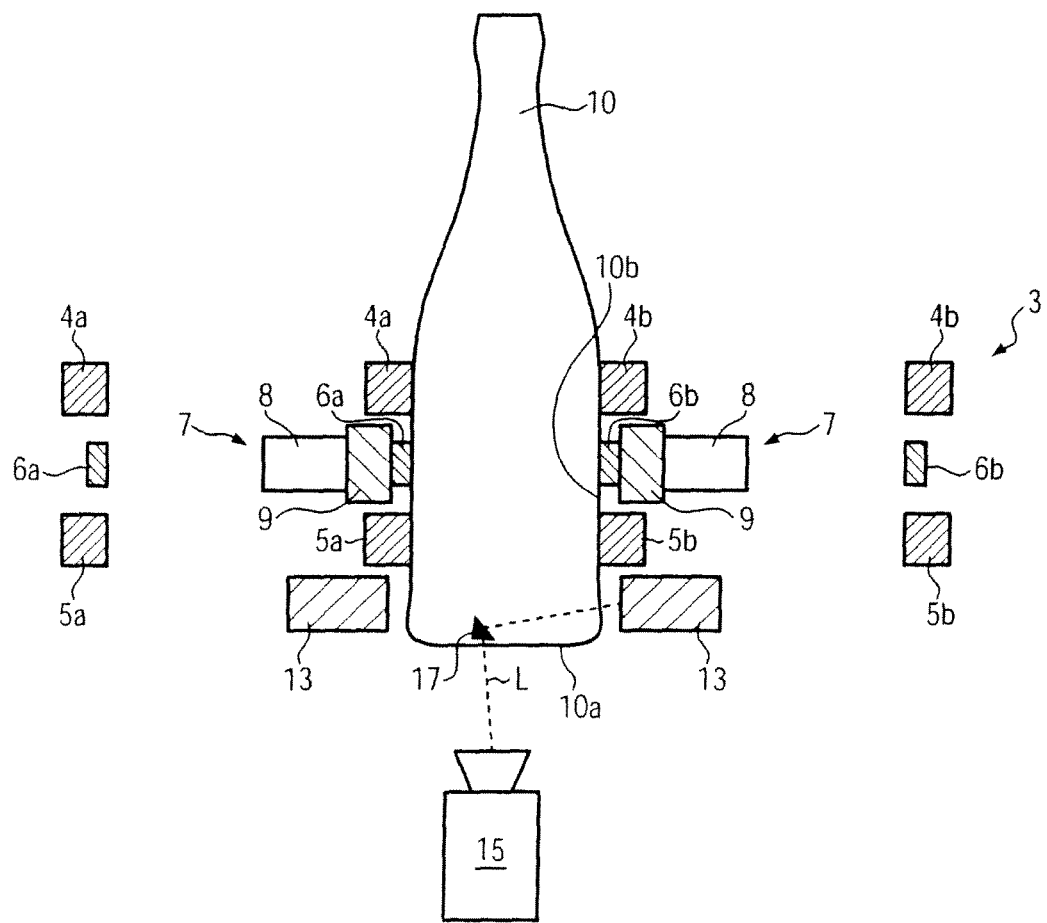
FIG. 2 a schematic cross-section through the device from FIG. 1 along the sectional line A-A.

As can be seen from FIGS. 1 and 2, the inspection device 1 according to the disclosure is designed as a linear machine with a linear transport section 2 and comprises a transport device 3 with an upper and a lower pair of guide belts 4a,b and 5a,b, whereby abutments for the guide belts 4a,b and 5a,b in the region of the transport section 2 have been omitted for the sake of clarity and the associated deflection rollers are only indicated in FIG. 1. An additional pair of transmission belts 6a,b is provided between the guide belts 4a,b and 5a,b, arranged essentially parallel to them and running together with them (hidden in the plan view by the upper guide belts 4a,b). The additional belts are a constituent part of a vibration device 7 with stationary vibrators 8 and slide rails 9 and they provide the transfer of vibration to the filled containers 10, such as for example glass or plastic bottles, which are to be inspected.

The guide belts 4a,b and 5a,b each hold at least one container 10 off the floor and transport it through a light corridor 11 consisting of two oppositely situated, sideward illumination units 13, past inspection cameras 15, which take dark-field images of the container bottom 10a or of foreign bodies 17 optionally present on it, such as for example glass splinters.

The containers 10 are passed to the inspection device 1 via a first conveyor belt 18 and carried away by a second conveyor belt 19 and transferred to a diversion device 21, such as a conventional pusher, for diverting faulty containers 10. The device also comprises a control and evaluation unit 23 for controlling the cameras 15, for evaluating the image data produced by the cameras 15 and for controlling the diversion device 21 on the basis of the inspection results. However, separate units can also be provided for this.

The vibration device 7 is in contact with the container 10 on both sides and transfers the oscillations through the container wall 10b and optionally to foreign bodies 17 located on the container bottom 10a, by means of which they are set in motion. The vibration device 7, double-sided with regard to the transport direction, facilitates a particularly effective transfer of vibrations to the container 10. However, it would also be possible to provide the vibration device 7 only on one side of the transport section 2. The inspection device 1 is also suitable for rotationally unsymmetrical containers 10, particularly for those with sectionally flat lateral faces 10b, on which the transmission belts 6a,b can contact over a large area, such as for example as with an essentially rectangular container cross-section.

The vibration device 7 is preferably supported vibration-damped on the inspection device 1 so that vibrations are selectively transferred to the container 10.

The vibration device 7 comprises at least one vibrator 8, for example in the form of a motor with an unbalance, as well as a slide strip 9 and/or a roller mechanism 9' (not illustrated) via which each of the transmission belts 6a,b runs under low friction. The slide strip 9 can for example be produced in a plastic with a low coefficient of friction, such as PTFE. The slide strips 9 or roller mechanisms 9' and/or the vibrators 8 could be tensioned by a spring force and press the transmission belts 6a,b against the container 10 in order to ensure a good transfer of the vibration. It is also conceivable that the vibration transfer is improved by a (not illustrated) moistening device at the contact point between the transmission belts 6a,b and the container 10.

The vibrator 8 preferably produces frequencies in the range between 10 and 50 kHz, in particular between 20 and 40 kHz, preferably at 30 kHz. Frequencies above the audible frequency range are particularly advantageous. If required, vibrators 8 could also be combined with different frequencies. The number of vibrators 8 can deviate from the illustrated example.

The transmission belts 6a,b are preferably produced from a material which transfers vibrations in the frequency range of the vibrator 8 particularly well to the container 10.

In contrast the guide belts 4a,b and 5a,b preferably contain a material which damps oscillations particularly well in the frequency range of the produced vibrations. Expediently, a damping layer can be provided on the belts 4a,b and 5a,b, for example a foam layer, in particular on the side facing the container 10.

The illumination units 13 comprise for example a plurality of light emitting diodes arranged one behind the other in the transport direction and are arranged on both sides of the transport section 2 with preferably the same distance to the container 10, in particular in the immediate vicinity of the container bottom 10a. In order to irradiate particles 17 in the vicinity of the bottom particularly effectively, the illumination units 13 are preferably arranged below the lower guide belts 5a,b. A position between the lower guide belts 5a,b and the transmission belts 6a,b would also be possible.

With the illumination units 13 directed light of different wavelengths, e.g. infrared, can be coupled into the inside of the filled containers 10 through the container side wall 10b. In the illumination units 13 a mixed arrangement of light-emitting diodes is conceivable, whereby single light-emitting diodes can be operated selectively with a certain wavelength according to the type of container and/or type of filling material. The illumination units 13 preferably emit continuous light in order to be able to acquire the image at any point in time. However, synchronous pulsed illumination units 13 are also conceivable with the cameras 15.

The cameras 15 are positioned such that the images of the containers 10, held above the ground, can be taken from underneath. The cameras 15 are expediently focused on the container bottom 10a or on a region slightly above the container bottom 10a in which the foreign bodies 17 may be present. In the imaging beam path deflection mirrors (not illustrated) could be provided for sideward beam deflection, for example by 90°, so that the cameras 15 are not arranged directly below the transport section 2, but are aligned to the side in order to prevent soiling and/or damage to the cameras 15.

The image areas of the cameras 15, the number of which is not restricted to the illustrated example, overlap so that a contiguous sequence of single images of the container bottom 10a can be produced. To achieve this the cameras 15 are triggered by the control and evaluation unit 23 in a suitable manner. The image data can be acquired, for example, by a 4-to-1 frame-grabber with which four cameras 15 are connected to a common computing processor of the control and evaluation unit 23. However, also just one camera 15 can be provided.

The control and evaluation unit 23 evaluates only a part of the image data of a single shot, namely an evaluation region ROI (Region Of Interest) (not illustrated) assigned to the bottle bottom 10a, for example a round-shaped image section. This means that the control and evaluation unit 23 only searches in the evaluation region ROI for moving structures or foreign bodies 17. This reduces the time required for the evaluation of a single shot and increases the number of possible shots per container inspection. In this way the probability that a light reflection on a foreign body 17, such as indicated in FIG. 2 by the dashed line L, can be registered or detected increases and thus too the accuracy or the reliability of the foreign body detection.

With the inspection device according to the disclosure the following method can be employed:

The filled containers 10 to be inspected are continuously fed from the first conveyor belt 18, pass continuously one after the other above the floor through the linear transport section 2 and are subjected to vibrations in the kilohertz range by the vibration device 7. Particles 17 in the vicinity of the bottom are set into motion by the oscillations and jump around on the container bottom 10a. In doing this they deflect the sidewards incident light to the cameras 15 which take triggered images of the container bottom 10a which are passed on to the control and evaluation unit 23. Here, image sections, in particular the evaluation regions ROI corresponding to the container bottom 10a of the camera images of a container 10 are compared to one another. Image differences in the evaluation region ROI are detected as moving particles and the faulty container 10 is diverted so that only fault-free containers 10 are passed for further processing.

In comparison to rotary machines the device 1 according to the disclosure is significantly more compact and more economical. Also rotationally unsymmetrically shaped bottles can be inspected in this way. The detection of foreign bodies 17 is more accurate and more reliable than with conventional inspection devices of the linear running type.

The invention claimed is:

1. Inspection device for detecting foreign bodies present in a filled container in a vicinity of a container bottom, comprising:
   a) at least one inspection camera arranged such that it can take dark-field images of the container bottom from below;
   b) a transport device for the at least section-by-section linear transport of the container;
   c) at least one vibration device for vibrating the container and setting the foreign bodies in motion; and
   d) at least one illumination device located below the transport device and below the vibration device, wherein the illumination device irradiates the container sideways such that the foreign bodies in the vicinity of the container bottom are irradiated.

2. Inspection device according to claim 1, wherein the vibration device comprises at least one vibrator for producing vibrations and a circumferentially running transmission belt for transferring the vibrations to the container.

3. Inspection device according to claim 2, wherein the vibrator is a motor with an unbalance.

4. Inspection device according to claim 2, wherein the vibration device comprises a slide rail and/or a roller unit which is in contact with the vibrator and the transmission belt.

5. Inspection device according to claim 1, wherein at least two vibration devices are provided which act on a side wall of the container from essentially opposite directions.

6. Inspection device according to claim 1, wherein the transport device comprises an upper and a lower pair of guide belts which hold the container off the ground in each case and the vibration device is set up such that it transfers vibrations to the container between at least one upper and one lower guide belt.

7. Inspection device according to claim 6, wherein the guide belts damp oscillations at an oscillation frequency of the vibration device.

8. Inspection device according to claim 1, wherein at least two inspection cameras are arranged one after the other in relation to the transport direction of the transport device and the image areas of the inspection cameras overlap.

9. Inspection device according to claim 1, wherein the illumination device is continuous light source.

10. Inspection device according to claim 1, wherein at least two illumination devices are provided which from a light corridor illuminating a container on both sides.

11. Inspection device according to claim 1, and an evaluation unit for the detection of foreign bodies through the comparison of image data from the inspection camera and a diversion device for diverting faulty containers.

12. Inspection method for the detection of foreign bodies present in a filled container in a vicinity of a container bottom, comprising:
   a) linear transporting the container at least section-by-section with a transport device;
   b) vibrating the container side wall with a vibration device to set foreign bodies into motion located on the container bottom;
   c) irradiating the container sideways with an illumination device located below the transport device and below the vibration device such that the foreign bodies in the vicinity of the container bottom are irradiated; and d) acquiring light which has been deflected on the foreign bodies and taking dark-field images of the container bottom from below.

13. Inspection method according to claim 12, wherein triggered dark-field single shots of the container bottom are taken in step d) and:

e) evaluating the acquired image data, wherein an image section is assigned in each case to the container bottom as an evaluation region and image data from the assigned evaluation regions are compared with one another to detect foreign bodies as differences in the compared image data; and f) rejecting the container if at least one foreign body has been detected in it.

\* \* \* \* \*